(12) United States Patent
Olson

(10) Patent No.: US 6,433,216 B1
(45) Date of Patent: Aug. 13, 2002

(54) NAPHTHYLOXYALKYL(METH)ACRYLATES WITH HIGH REFRACTIVE INDICES AND LOW GLASS TRANSITION TEMPERATURES

(75) Inventor: David B. Olson, Marine on St. Croix, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/024,058

(22) Filed: Dec. 17, 2001

Related U.S. Application Data

(62) Division of application No. 09/605,462, filed on Jun. 28, 2000.

(51) Int. Cl.[7] ............................................. C07C 69/52
(52) U.S. Cl. ....................................................... 560/221
(58) Field of Search .......................................... 560/221

(56) References Cited

PUBLICATIONS

Hans et al ,Syn. and Comp. structural investigation of crystalline and liquid crystalline phases, Jul. 1990, 8(1), p. 95–108.*

* cited by examiner

*Primary Examiner*—Paul J. Killos
*Assistant Examiner*—Taylo V. Oh
(74) *Attorney, Agent, or Firm*—Stephen W. Buckingham

(57) ABSTRACT

Naphthyloxyalkyl(meth)acrylate monomers having a high refractive index and whose respective homopolymer has a low glass transition temperature.

5 Claims, No Drawings

NAPHTHYLOXYALKYL(METH)ACRYLATES WITH HIGH REFRACTIVE INDICES AND LOW GLASS TRANSITION TEMPERATURES

CROSS-REFERENCE RELATED TO OTHER APPLICATIONS

This application is a divisional of Application Ser. No. 09/605,462, filed Jun. 28, 2000, pending.

TECHNICAL FIELD

This invention relates to naphthyloxyalkyl(meth)acrylate compounds with a high refractive index and whose respective homopolymer has a low glass transition temperature.

BACKGROUND

Adhesives or coatings used in optical applications preferably have a refractive index closely matched to the refractive index of a substrate to which they are applied. The matched refractive indices reduce glare and reflectance at the interface between the substrate and coating materials and enhance the optical performance of the construction.

Polymeric substrate materials typically used in optical applications have refractive indices of about 1.48 to about 1.65, such as, for example, polymethyl(meth)acrylate (1.489), polycarbonate (1.585), and polyethylene terephthalate (1.64). However, many polymeric coatings and adhesives intended for application to these substrates have refractive indices that differ substantially from the refractive indices of the substrates. The mismatched refractive indices may cause glare and reflectance at the interface between the materials.

Reactive chemical monomers can be used, alone or in combination with other materials, to produce adhesives and coatings with high indices of refraction. However, these adhesive and coating compositions may have other less desirable physical and chemical properties. For example, certain naphthalene derivatives of Formula 1 below have an index of refraction of about 1.57–1.58:

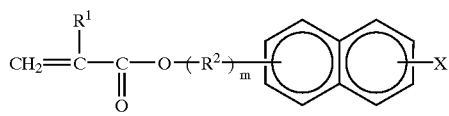

Formula 1 wherein $R^1$ is H or $CH_3$, $R^2$ is $CH_2CH_2O$ or $CH(CH_3)CH_2O$, X is H, and m is 1. While the refractive index of the monomers in Formula 1 may match well with polymeric substrates commonly used in optical applications, homopolymers made from known compounds of this type typically have a glass transition temperature (Tg) of about 25 to about 40° C. For this reason, polymers including these monomeric units would be expected to be essentially non-tacky at or near room temperature (about 20 to about 30° C.), which limits their usefulness in optical adhesives and flexible coatings.

SUMMARY

In one aspect, the invention is a naphthyloxyalkyl(meth) acrylate monomer with an index of refraction of greater than about 1.55 and a glass transition temperature of its respective homopolymer of less than about 10° C. The naphthyloxyalkyl(meth)acrylate monomers include a (meth) acrylate functional group and a naphthyloxy functional group linked by an alkyl functional group.

The preferred naphthyloxyalkyl(meth)acrylate monomers of the invention have the general Formula 2:

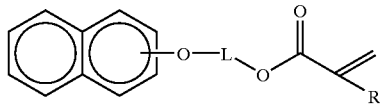

Formula 2 wherein L is a straight chain or branched alkyl group containing greater than 5 carbon atoms, preferably from about 6 to about 8 carbon atoms, and R is H or $CH_3$.

In a second aspect, the invention is a polymerizable composition containing the monomer of Formula 2. The polymerizable composition can contain one or more other compatible comonomers.

In a third aspect, the invention is a polymer or polymeric material including a chemical segment of Formula 3:

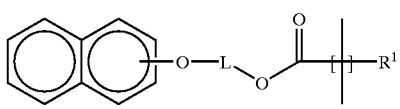

Formula 3 wherein L is a straight chain or branched alkyl group containing greater than 5 carbon atoms, preferably from about 6 to about 8 carbon atoms, and $R^1$ is H or $CH_3$. The polymers with the monomeric segment of Formula 3 have a low glass transition temperature of less than about 10° C., and are well suited for use in optical adhesives and flexible coating compositions. The adhesives and coating compositions made from the monomers of the invention would be expected to reduce glare and reflectance when applied to a polymeric substrate with a similarly high refractive index.

In a fourth aspect, the invention is an optical element including a composition with the polymer or polymeric material with the segment of Formula 3.

In a fifth aspect, the invention is an optical device including a composition with the polymer or polymeric material with the segment of Formula 3.

In a sixth aspect, the invention is a method for reducing glare and/or reflectance on a substrate that includes coating the substrate with a composition with the polymer or polymeric material with the segment of Formula 3.

The details of one or more embodiments of the invention are set forth in the description below. Other features, objects, and advantages of the invention will be apparent from the description and from the claims.

DETAILED DESCRIPTION

The invention is a naphthyloxyalkyl(meth)acrylate monomer with a high refractive index and whose respective homopolymer has a low glass transition temperature. The monomers have specific index of refraction, melting point, and viscosity properties that are particularly suited for use in polymeric materials intended for application to a substrate in an optical element or an optical device.

As used within the present description, "monomer" refers to a monomer on an individual (i.e., molecular) scale, and also to a composition of such monomers on a macroscopic scale such that the composition can be described as having a physical state of matter (e.g., liquid, solid, etc.) and physical properties (e.g., melting point, viscosity, glass transition temperature (of a polymeric form), and index of refraction).

The naphthyloxyalkyl(meth)acrylate monomers of the invention have an index of refraction of at least about 1.54, preferably between about 1.54 and 1.56. "Index of refraction," or "refractive index," refers to the absolute refractive index of a material (e.g., a monomer), which is understood to be the ratio of the speed of electromagnetic radiation in free space to the speed of the radiation in that material, with the radiation being of sodium yellow light at a wavelength of about 583.9 nanometers (nm). Index of refraction can be measured by known methods, and is generally measured using an Abbe Refractometer.

Homopolymers of the naphthyloxyalkyl(meth)acrylate monomers of the invention have a Tg below about 10° C., preferably less than about 7° C., and most preferably less than about 5° C. "Glass transition temperature," (Tg), is the temperature range over which a thermoplastic polymer changes from a brittle, glass state to a plastic state. Glass transition temperature of a composition can be measured by methods known in the art, such as Differential Scanning Calorimetry (DSC), modulated DSC (MDSC), or Dynamic Mechanical Analysis (DMA).

The naphthyloxyalkyl(meth)acrylate monomers include a (meth)acrylate functional group and a naphthyloxy functional group linked by an alkyl functional group.

The alkyl group is a divalent organic hydrocarbon group. The alkyl group, which is preferably unsubstituted, can be straight or branched and includes greater than 5 carbon atoms, more preferably from 6 to 8 carbon atoms. The size of the alkyl group can affect the physical properties of the monomer and a polymer prepared from the monomer including, for example, the refractive index of the monomer and the refractive index and glass transition temperature of a polymer prepared from the monomer. While not wishing to be bound by any theory, a relatively larger alkyl group may result in a monomer or a polymer with a relatively lower index of refraction compared to an otherwise similar monomer or polymer having a relatively smaller alkyl group. Again, while not wishing to be bound by any theory, relatively larger or more branched alkyl groups may provide a monomer which, when polymerized, has a relatively lower Tg compared to a polymer prepared from otherwise similar monomers having relatively smaller or less branched alkyl groups.

The naphthyloxy group in the monomer of the invention is also preferably unsubstituted.

The (meth)acrylate group in the monomer of the invention can be prepared by methods well known to those skilled in the art. The naphthyloxy alkanol intermediates can be esterified with (meth)acyloyl chloride using a suitable base. They can also be prepared by condensation with (meth)acrylic acid, or by transesterification using, for instance, methyl (meth)acylate. Suitable inhibitors can be added to the reactions during the synthesis of the monomers to prevent premature polymerization of the monomers.

Examples of useful naphthyloxy alkyl acrylate monomers include those with the structure of Formula 2:

Formula 2

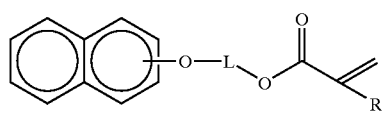

wherein L is a straight chain or branched alkyl group containing greater than 5 carbon atoms, preferably from about 6 to about 8 carbon atoms, and R is H or CH$_3$.

Examples of useful monomers include 6-(1-naphthyloxy)-1-hexylacrylate, wherein the oxyalkylacrylate group is located at the 1 or α position on the naphthalene ring structure and the alkyl unit has 6 carbon atoms. This monomer, shown below in Formula 4, has a refractive index of about 1.556 and the Tg of its homopolymer is about 3° C.

Formula 4

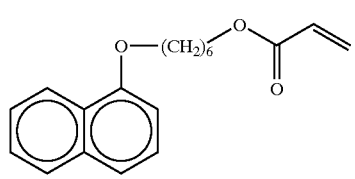

Another preferred monomer is 6-(2-naphthyloxy)-1-hexylacrylate, wherein the oxyalkylacrylate group is located at the 2 or β position on the naphthalene ring structure and the alkyl unit has 6 carbon atoms. This monomer, shown below in Formula 5, has a refractive index of about 1.553 and the Tg of its homopolymer is about 6° C.

Formula 5

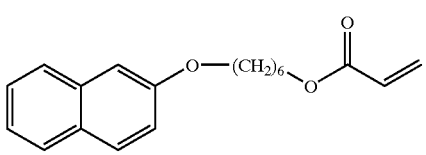

Another preferred monomer is 8-(1-naphthyloxy)-1-octylacrylate, wherein the oxyalkylacrylate group is located at the 1 or α position on the naphthalene ring structure and the alkyl unit has 8 carbon atoms. This monomer, shown below in Formula 6, has a refractive index of about 1.547 and the Tg of its homopolymer is about −49° C.

Formula 6

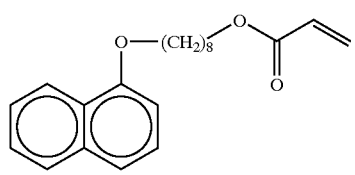

The monomer of the invention, alone or in combination with materials such as other unsaturated polymerizable comonomers, can be included in a polymerizable composition that can be polymerized or co-polymerized to produce useful polymers or copolymers. As used within the present description, the term "polymerizable" refers to chemical compounds such as monomers and oligomers, etc., and chemical compositions, capable of polymerizing or copolymerizing (e.g., via unsaturated moieties) to produce a higher molecular weight materials such as an oligomer, polymer, prepolymer, or polymeric material. The terms "polymer" and "polymeric material" are used interchangeably to refer to materials prepared from the reaction of one or more polymerizable materials, e.g., one or more polymerizable monomer, oligomer, polymer, or prepolymer, etc., to produce a dimer, trimer, oligomer, copolymer, homopolymers, etc.

The polymers and polymeric materials include a chemical segment of Formula 3:

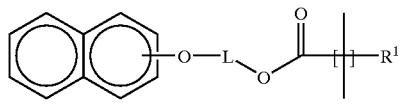

Formula 3 wherein L is a straight chain or branched alkyl group, preferably containing greater than 5 carbon atoms, preferably from about 6 to about 8 carbon atoms, and $R^1$ is H or $CH_3$.

Useful comonomers to be reacted with acrylic monomers such as the monomer described herein are known in the organic chemistry art, and can include any of a number of known and useful polymerizable moieties, e.g., vinyl, (meth)acrylate, N-vinyl, acrylic acid, methacrylic acid, allyl, acrylamide, acrylonitrile, etc. The comonomer can be mono- or multifunctional with respect to the unsaturated moiety, and where multifunctional, the unsaturated moieties need not be of identical chemistry.

Specific types of comonomers useful in the polymerizable composition can include (meth)acrylate-functional comonomers such as butyl (meth)acrylate, as well as vinyl comonomers such as methyl styrene. The particular comonomers included in any given polymerizable composition, their molecular weight or weights, and the included amounts of each, can be chosen according to various factors such as the desired nature and properties of the polymerizable composition and the desired properties of the polymer or polymeric material to be prepared therefrom (e.g., index of refraction, glass transition temperature, melting point, viscosity, etc., of the polymerizable composition or polymeric material).

The polymerizable composition can also contain other ingredients that, as will be appreciated by those skilled in the art of polymeric materials, can be useful in such a polymerizable composition. For example, the polymerizable composition might contain a crosslinking agent, one or more surfactants, pigments, fillers, polymerization inhibitors, or other ingredients that can be useful within a polymerizable composition or an optical product. Such ingredients can be included in the composition in amounts known to be effective for their respective purposes.

A crosslinking agent can be useful to increase the glass transition temperature of the polymer resulting from crosslinking the polymerizable composition.

Polymeric beads, inorganic fillers, and/or pigments can be added to the polymerizable composition in order to improve processing, to impart slip and scratch resistance to the polymerized material, or to affect optical properties of the polymerized material. Examples of useful polymeric beads include those made of polystyrene, polyacrylates, copolymers of styrene and acrylates, polyethylene, polypropylene, polytetrafluoroethylene, or combinations thereof. Examples of inorganic fillers and pigments include solid or hollow glass beads, silica, zirconia, aluminum trihydroxide, and titanium dioxide.

Polymerization of the polymerizable composition can be accomplished by known and usual means, such as heating in the presence of a free-radical initiator, irradiation with electromagnetic radiation such as ultraviolet or visible light in the presence of suitable photoinitiators, and by electron beam.

Polymeric materials (i.e., homopolymers or copolymers) prepared from the monomer of the invention have a Tg below about 10° C., as well as a refractive index greater than about 1.54. This makes the polymers particularly well suited to use as coatings and adhesives on polymeric substrates used in optical elements and optical devices, such as, for example, polymethylmethacrylate (PMMA), polycarbonate (PC), and polyethyleneterephthalate (PET). For example, as described in copending U.S. application Ser. No. 09/605,500 incorporated by reference, the polymers prepared from the monomers of the invention may be used to make pressure-sensitive adhesives to be applied to a substrate in an optical device. Polymers prepared from the monomers of the invention may also be used as a coating for an optical element in an optical device.

Compared to conventional polymers, the polymers made from the monomers of the invention have refractive indices that are more closely matched with the refractive indices of polymeric substrates commonly used in optical elements and devices. This refractive index match reduces glare and reflectance at any optical interface between the substrate and the polymers, so the polymers made from the monomers of the invention may be used as part of a method for reducing glare and/or reflectance on a substrate. The method includes coating the substrate with a composition with the polymer or polymeric material with the fragment of Formula 3.

The term "glare" as used herein means the average reflectance over a range of about 400 to about 700 nm. The term "reflectance" means the fraction of incident flux on a surface that is returned to into the same hemisphere whose base is the surface and which contains the incident radiation.

The invention will be more fully appreciated with reference to the following non-limiting examples in which the reaction components are given as grams (g) used or as weight percents (wt %), based on the total weight of the reaction mixtures which are nominally 100 wt %. Dimensions in English units are nominal and conversion to Metric units is approximate.

EXAMPLE 1

Synthesis of 6-(1-naphthyloxy)-1-hexyl acrylate (1-NOHA)

A one-liter three-neck flask was equipped with a mechanical stirrer, temperature probe, and a condenser. The following reagents were added: 50 g 1-naphthol, 312 g deionized water, 5.2 g sodium iodide, and 55.4 g sodium hydroxide (50% in water). The mixture was heated to reflux. To the refluxing reaction 94.7 g 6-chloro-1-hexanol was added dropwise. through an addition funnel over a two-hour period. Heating at reflux was continued for an additional hour after completing the addition. Gas chromatography (GC) analysis showed less than 1% residual starting material.

The reaction was cooled to room temperature. 366 g t-butyl methyl ether was added. The reaction mixture was stirred, then poured into a separatory funnel and allowed o phase split. The aqueous phase was removed and the organic phase washed with 6.9 g concentrated HCl in 125 g deionized water, then with 6.1 g NaCl in 125 g deionized water. The remaining solvent was stripped from the product using a rotary evaporator.

The product was distilled at a pot temperature of 220–260° C. and a head temperature of 200–230° C. at 0.1–0.2 mm Hg. This procedure yielded 63.5 g of a light brown, somewhat viscous liquid. GC showed it was at least 98% pure 6-(1-naphthyloxy)-1-hexanol.

A one-liter three-neck flask was equipped with a mechanical stirrer, temperature probe, and Dean-Stark trap with condenser was charged with the following reagents: 60 g 6-(1-naphthyloxy)-1-hexanol, 226 g toluene, 2.5 g para-toluene sulfonic acid, 21.2 g acrylic acid, 0.027 g hydroquinone, and 0.03 g 4-methoxyphenol. The mixture was heated to reflux, collecting the water, which evolved in the Dean-Stark trap. After three hours, thin layer chromatography showed the reaction was complete (i.e., no starting material remained).

The reaction was cooled to room temperature and 132 g deionized water was added. The mixture was put into a separatory funnel, shaken and allowed to phase split. The aqueous layer was removed and the organic phase was washed with 0.3 g concentrated HCl in 44 g deionized water, then with 1.3 g sodium carbonate in 44 g deionized water, and then with 1.4 g sodium chloride in 44 g deionized water. The remaining solvent was stripped using a rotary evaporator. The crude product residue was passed through a flash silica gel column eluting with a mixture of ethyl acetate/heptanes (5/95). The product fractions were collected and the solvent stripped using a rotary evaporator. The light greenish oil product crystallized on standing to give 45 g of off-white crystals with a melting point of 37–39° C. GC and $^{13}$C NMR analysis confirmed the product to be greater than 99% pure 6-(1-naphthyloxy)-1-hexyl acrylate (1-NOHA).

The refractive index of the 1-NOHA was 1.556 as measured using an Abbe Refractometer, made by Erma Inc. of Tokyo, Japan and distributed by Fisher Scientific.

Homopolymer was prepared by charging a 120 ml bottle with 2.0 g 1-NOHA monomer, 10 g ethyl acetate, and 0.06 g of a catalyst, available from E. I. DuPont De Nemours and Co., Wilmington, Del., under the trade designation VAZO 64. The bottle was deoxygenated by purging with nitrogen at a flow rate of 1 liter per minute for 35 seconds. The bottle was then sealed and placed in a rotating water bath at 55° C. for 24 hours to effect essentially complete polymerization. Polymer films were prepared by casting the polymer solution in an aluminum pan and evaporating the solvent in a 65° C. oven. Glass transition temperatures (Tg) were determined using a differential scanning calorimeter (DCS-7) manufactured by Perkin Elmer, Norwalk, Conn. A 10 mg polymer sample was heated at a rate of 20° C./minute, cooled at a rate of 40° C./minute, and then reheated at 20° C./minute. The Tg was calculated on the second heating cycle, and was calculated to be 6° C.

EXAMPLE 2

Synthesis of 8-(1-naphthyloxy)-1-octylacrylate (1-NOOA)

A 500 ml three-neck flask was equipped with a mechanical stirrer, temperature probe, and a condenser. The following reagents were added: 25 g 1-naphthol, 156 g deionized water, 2.6 g sodium iodide, and 27.7 g sodium hydroxide (50% in water). This mixture was heated to reflux. To the refluxing reaction was added 57.1 g 8-chloro-1-octanol dropwise through an addition funnel over a two-hour period. Heating at reflux was continued for one additional hour after completing the addition. GC showed less than 1% residual starting material.

The reaction was cooled to room temperature, and 207 g chloroform was added. The mixture was stirred, then poured into a separatory funnel, and allowed to phase split. The upper aqueous phase was separated out, and the organic phase was washed with 3.4 g concentrated HCl in 62 g deionized water, then with 3.0 g NaCl in 62 g deionized water. The solvent was stripped from the product using a rotary evaporator.

The product was then distilled, first removing residual 8-chloro-1-octanol at a head temperature of about 100° C. and 0.2 mm Hg. The product distilled at a head temperature of 180–200° C. at 0.1 mm Hg. About 17 g of 8-(1-naphthyloxy)-1-octanol was collected, which was a light orange color.

A 250 ml three-neck flask was equipped with a mechanical stirrer, temperature probe, and Dean-Stark trap with condenser. The following reagents were added: 14 g 8-(1-naphthyloxy)-1-octanol, 118 g toluene, 0.5 g para-toluene sulfonic acid, 4.5 g acrylic acid, 0.006 g hydroquinone, and 0.006 g 4-methoxyphenol. The mixture was heated to reflux, and the water that evolved was collected in the Dean-Stark trap. After three hours, thin layer chromatography showed that the reaction was complete.

The reaction was cooled to room temperature and 27 g deionized water was added. The mixture was shaken well in a separatory funnel, phase split, and the aqueous layer was removed. The organic phase was washed sequentially with 0.1 g concentrated HCl in 10 g deionized water, then with 0.3 g sodium carbonate in 10 g deionized water, then with 0.3 g sodium chloride in 10 g deionized water. The solvent was stripped using a rotary evaporator, and the crude product residue was passed through a flash silica gel column eluting with methylene chloride. The product fractions were collected and solvent stripped using a rotary evaporator, finishing by pulling on the flask with a vacuum pump to remove the last traces of solvent.

The light yellow oil product crystallized on standing to give 12 g of a wet semi-solid. GC and $^{13}$C NMR confirmed that the product was greater than 99% pure 8-(1-naphthyloxy)-1-octylacrylate (1-NOOA).

The refractive index of the 1-NOOA was 1.547 as measured using an Abbe Refractometer, made by Erma Inc. of Tokyo, Japan and distributed by Fisher Scientific.

Homopolymer was prepared as described in Example 1 except 1-NOOA was used instead of 1-NOHA. The Tg of the homopolymer was −49° C.

A number of embodiments of the invention have been described. Nevertheless, it will be understood that various modifications may be made without departing from the spirit and scope of the invention. Accordingly, other embodiments are within the scope of the following claims.

What is claimed is:

1. A polymerizable composition comprising the monomer of Formula 2, wherein L is a straight chain or branched alkyl group with greater than 5 carbon atoms and R is H or CH$_3$

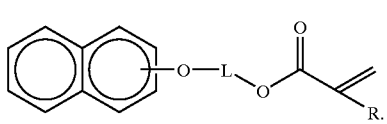

Formula 2

2. A polymer comprising the reaction production of one or more monomer(s) of Formula 2

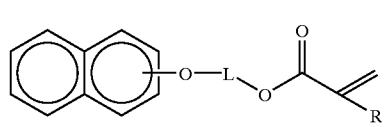

Formula 2 wherein L is a straight chain or branched alkyl group with greater than 5 carbon atoms and R is H or $CH_3$, and optionally one or more comonomer(s), where the comonomer(s) has a polymerizable moiety selected from the group consisting of vinyl, (meth)acrylate, N-vinyl, acrylic acid, methacrylic acid, allyl, acrylamide, acrylonitrile, and mixtures thereof.

3. An optical element comprising the polymer of claim 2.

4. An optical device comprising an optical element, wherein the optical element comprises the polymer of claim 2.

5. A method for reducing glare on a substrate comprising applying to the substrate the polymer of claim 2.

* * * * *